United States Patent [19]

Castellini

[11] Patent Number: 5,087,198
[45] Date of Patent: Feb. 11, 1992

[54] DENTAL SURGERY APPARATUS CAPABLE OF SUPPLYING THREE SEPARATE FLUIDS TO CONNECTED INSTRUMENTS

[75] Inventor: Franco Castellini, Bologna, Italy
[73] Assignee: Castellini S.p.A., Bologna, Italy
[21] Appl. No.: 410,670
[22] Filed: Sep. 21, 1989

[30] Foreign Application Priority Data

Sep. 30, 1988 [IT] Italy ................. 3608 A/88

[51] Int. Cl.5 ............................. A61C 1/10; A61C 1/12
[52] U.S. Cl. ............................................ 433/80; 433/28
[58] Field of Search ................ 433/98, 99, 100, 27, 433/28, 80, 84, 85

[56] References Cited

U.S. PATENT DOCUMENTS

| | | | |
|---|---|---|---|
| 28,390 | 4/1975 | Staunt | 433/80 |
| 3,593,423 | 7/1971 | Jones et al. | 433/80 |
| 3,698,088 | 10/1972 | Austin, Jr. | 433/80 |
| 3,718,973 | 3/1973 | Slater et al. | 433/84 |
| 3,757,421 | 9/1973 | Kraft | 433/98 X |
| 4,145,813 | 3/1979 | Hall | 32/22 |
| 4,193,197 | 3/1980 | Kuris et al. | 433/82 |
| 4,215,476 | 8/1980 | Armstrong | 433/80 |
| 4,302,185 | 11/1981 | Hall | 433/84 X |
| 4,382,786 | 5/1983 | Löhn et al. | 433/28 X |
| 4,545,956 | 10/1985 | Ciszewski et al. | 422/28 |
| 4,752,444 | 6/1988 | Bowen et al. | 422/28 |

FOREIGN PATENT DOCUMENTS

| | | | |
|---|---|---|---|
| 0024255 | 2/1981 | European Pat. Off. | 433/98 |
| 0233847 | 8/1987 | European Pat. Off. | |
| 1222150 | 6/1960 | France . | |

Primary Examiner—Robert P. Swiatek
Assistant Examiner—Todd E. Manahan
Attorney, Agent, or Firm—Laff, Whitesel, Conte & Saret

[57] ABSTRACT

In dental surgery apparatus, provided with the usual compressed air and water circuits supplying power and spray to drills and other instruments, use is made of a reservoir from which to dispense physiological saline into a pipeline connecting with the main water supply circuit; upstream of the resulting connection, the respective lines carrying saline and spray water are controlled by a 3-way, 2-position valve that permits of alternating from one source of liquid to the other as required.

3 Claims, 2 Drawing Sheets

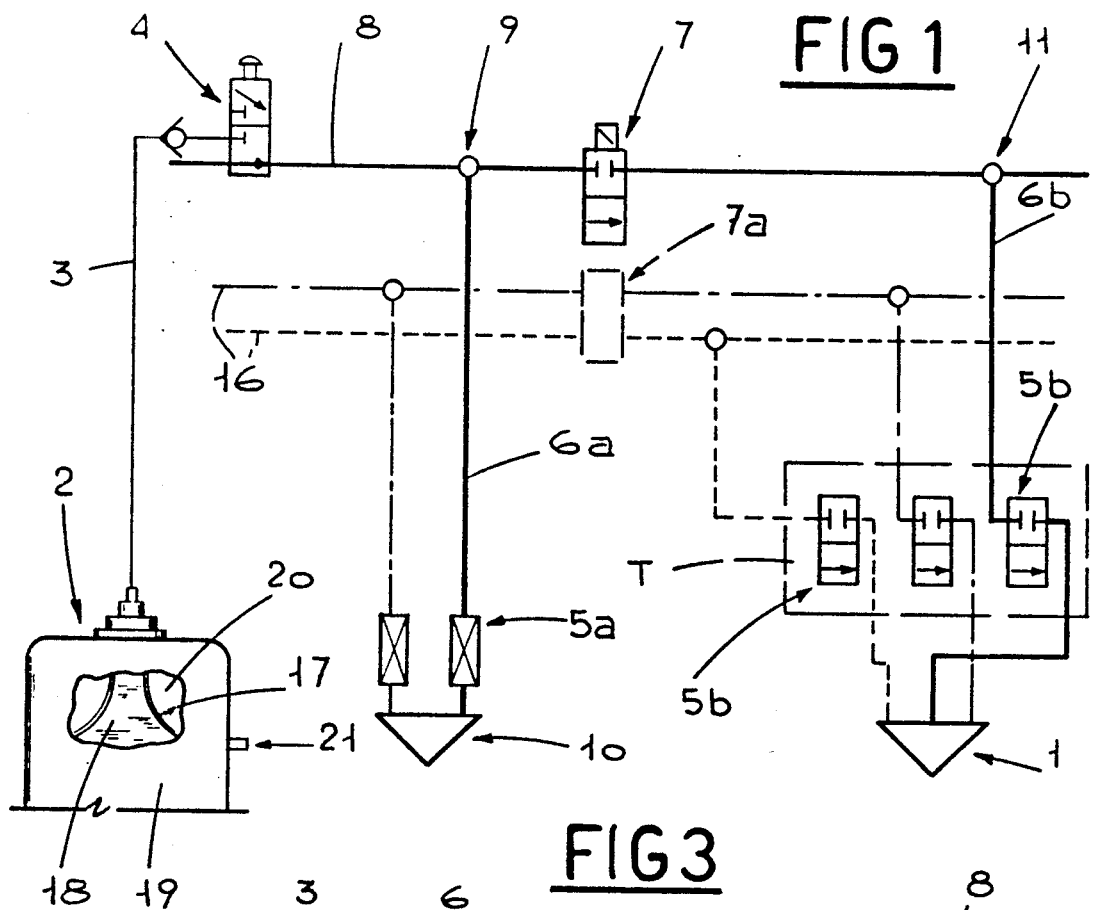
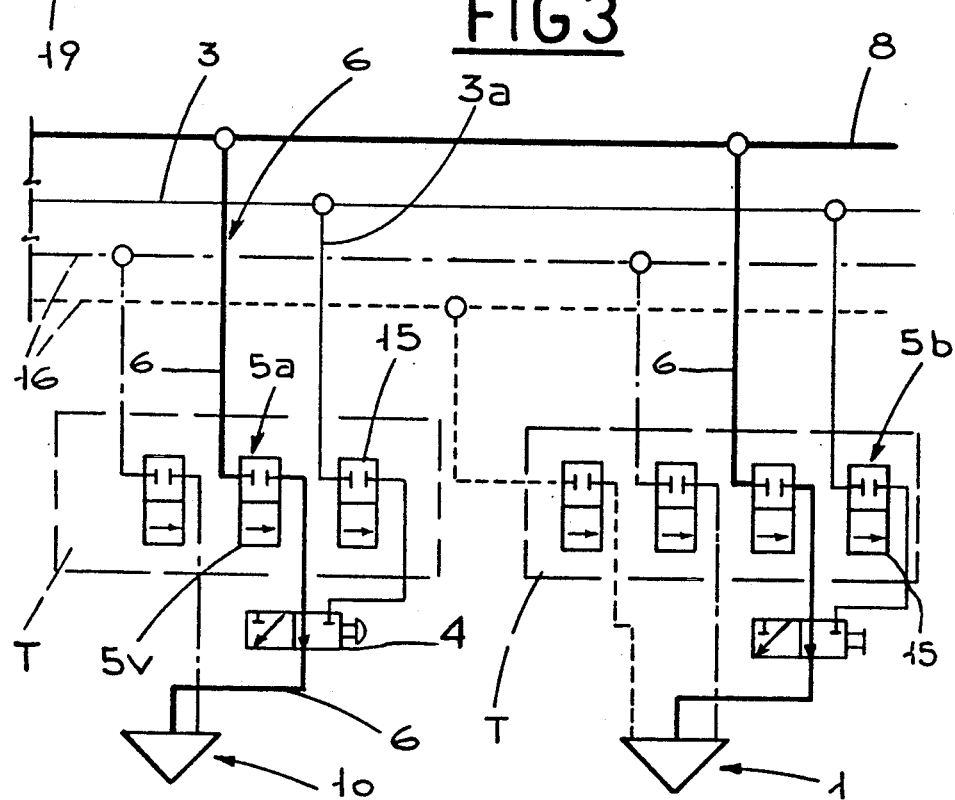

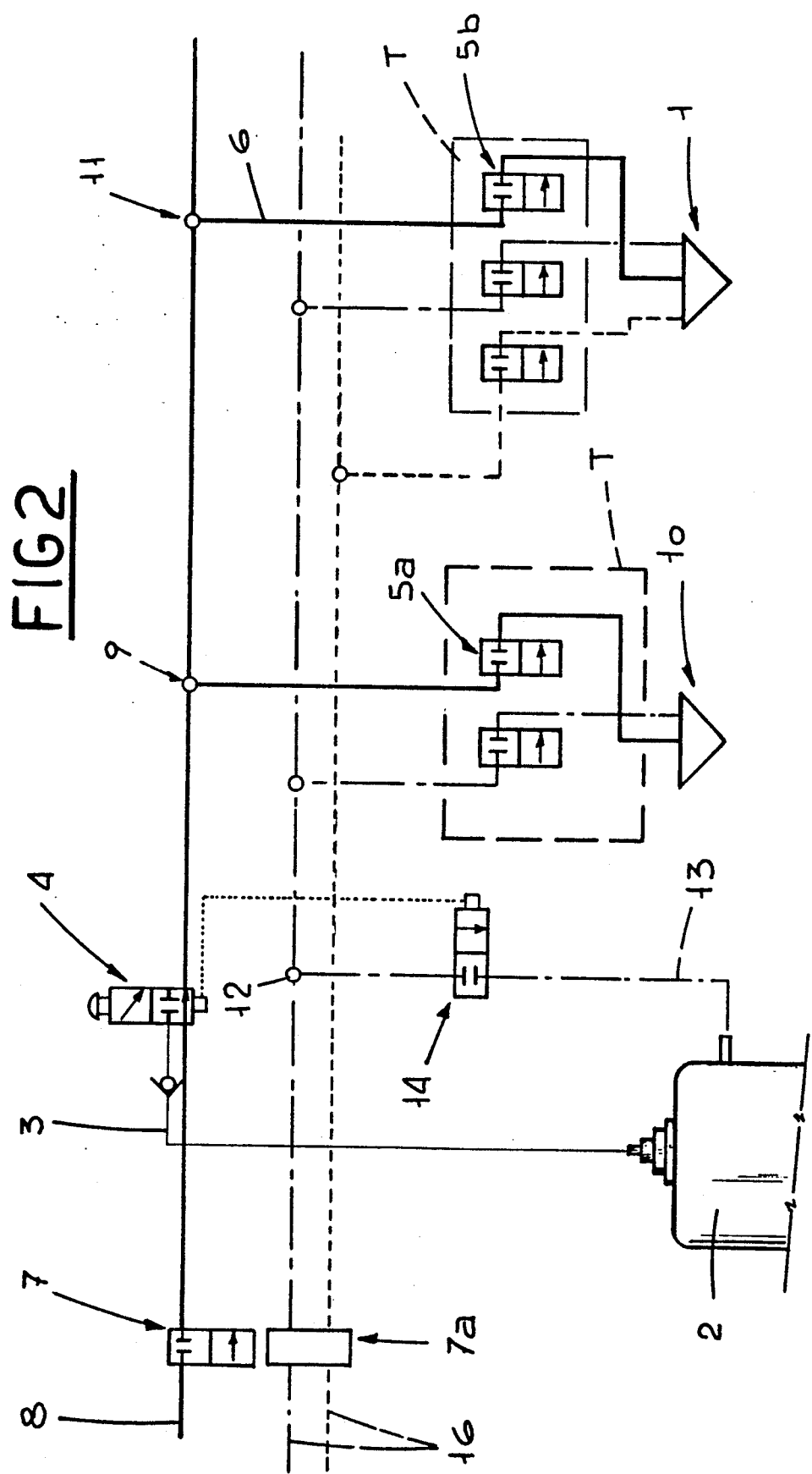

DENTAL SURGERY APPARATUS CAPABLE OF SUPPLYING THREE SEPARATE FLUIDS TO CONNECTED INSTRUMENTS

BACKGROUND OF THE INVENTION

The present invention relates to dental surgery apparatus provided with means by which instruments, connected to the apparatus, can be supplied with at least three distinct fluids, for example air and water, and in addition, a physiological, medical or other similar solution.

During the course of a session of dental treatment, the practitioner will often invest the treatment area with air and/or water, though only in the preparatory stages prior to commencing any surgical operation, or when inspecting the oral cavity. During surgery proper, either the practitioner or an assistant will flood the affected area with a physiological liquid in such a way as to cleanse tissue isotonically of any accumulating debris; the liquid most widely used is a 0.9% sterile solution of sodium chloride in distilled water.

The use of a physiological solution in surgery is essential at the present time in view of the fact that the water supplied to the instrument circuits is drawn directly from the local domestic main; notwithstanding the water from a typical domestic supply may be potable, it will be neither sterile nor physiological, and given that the area to be flooded is in effect an open wound, cannot be used without the risk of infection.

Conventionally, these physiological solutions are dispensed by means of an independent auxiliary instrument, whereas the basic surgery instruments (turbine and micro drive drills, chip blower etc.) are embodied with air and water circuits only, as discernible from numerous patent specifications pertinent to the art field in question, for example U.S. Pat. No. Re. 28,390.

Observing the drawings that accompany the U.S. patent specification in question, it will be seen that there are two parallel passages running through the handpiece of each instrument and terminating at its projecting end; these passages are connected with respective supplies of air and water, and converge substantially on the point of an attachment or bit fitted to the handpiece. Whilst the illustration in U.S. Pat. No. Re. 28,390 refers only to the turbine drill, the design of the handpiece remains substantially the same for the micro and the chip blower also, at least as far as the air and water supply passages are concerned.

Given the manner in which the various instrument handpieces available to the dentist are structured, as described above, and considering the frequency with which the physiological solution is applied, the need for a chairside assistant to be constantly in attendance is readily understandable; in effect, the absence of the assistant, even if moving away but momentarily to perform another task, dictates necessarily that the dentist discard the instrument currently in use, take up the tube from which the physiological solution is dispensed so as to flood the treatment area, replace the tube, and then take up the instrument required for continuation of the treatment.

Such a situation tends to prolong the duration of surgery, thus causing unease to patients by reason of their being kept in an essentially uncomfortable posture, and produces a certain disenchantment deriving from the laboriousness of the procedure. At the same time, the speed gained by enlisting the services of an assistant can be offset by a lack of first-time accuracy, resulting in the necessity for repeated applications of the solution.

Accordingly, the object of the invention is to embody dental surgery apparatus in such a way that a physiological solution can be supplied to the instruments attached to such apparatus, accurately and without delay, at any given moment.

SUMMARY OF THE INVENTION

The stated object is realized with dental surgery apparatus according to the present invention. Such apparatus is of the type provided with fluid circuits from which air and water are directed to a plurality of permanently connected instruments, a reservoir containing a supply of physiological or medical, healing or other similar solution, and a relative fluid line connecting the reservoir to the water supply circuit.

The apparatus disclosed also features three-way directional control over the water supply circuit and solution reservoir line at points upstream of their mutual junction, which can be switched to keep either one of the two fluid sources open at any given time.

One of the advantages afforded by the apparatus disclosed is that of simplicity in construction, gained by a convenient integration of the solution line and its switchable control facility into the existing fluid circuits of conventional apparatus.

BRIEF DESCRIPTION OF THE DRAWINGS

The invention will now be described in detail, by way of example, with the aid of the accompanying drawings, in which:

FIG. 1 provides a schematic representation of the essential components of apparatus according to the invention;

FIGS. 2 and 3 are further schematic representations of the apparatus, illustrating two variations on the embodiment shown in FIG. 1.

DESCRIPTION OF THE PREFERRED EMBODIMENTS

With reference to FIG. 1, apparatus according to the invention consists in a plurality of dental surgery instruments 1 (drills, chip blower, etc.) connected in conventional manner to circuits denoted 8 and 16 through which air and water are supplied to the relative handpieces.

Certain of these instruments 1, for example the turbine drill, connect with two air circuits (power and spray), whereas other instruments such as the chip blower 10, connect only with the spray air circuit 16.

It will be observed that the main water circuit 8 presents a first branch 9 from which a line 6a is taken to the chip blower 10, and further branches denoted 11 from which relative lines 6b are taken off to the remaining instruments 1. Conventionally, on-off means 7 are installed between the first and second branches 9 and 11, as in FIG. 1; such means 7 are pedal-controlled for the most part and operated directly by the user of the apparatus, generally in conjunction with similar means 7a controlling the air circuit 16.

With the exception of the water line 6a to the chip blower 10, the lines 6b branching to each of the various instruments 1 are controlled by relative on-off means 5b which open at the moment when the instrument is taken up for use; more exactly, such means take the form of solenoid valves 5b located in the instrument holder T of the apparatus, which excite only when the handpieces are removed from the holder and therefore remain closed as long as the relative instrument is not in use. In the case of the chip blower 10, on the other hand, on-off means 5a are embodied typically as mechanically operated valves located downstream of the handpiece and manipulated by the user.

Thus, with the exception of the chip blower 10, each instrument 1 comprises two different sets of on-off means 5b and 7 controlling the relative fluid circuits, of which the means 5b located farthest downstream along the flow direction are activated automatically on taking up the handpiece, and the means 7 upstream activated manually, or in effect, by depressing a pedal.

Apparatus according to the present invention is provided with a reservoir 2 containing a supply of physiological, medical, healing or other solution dispensed by way of a relative supply line 3 into the main water circuit 8.

The solution pipeline 3 and water supply circuit 8 are governed jointly by means 4, interlocked to a suitable control medium, that permit of blocking either one of the two sources at any given time. Operation of the means 4 in question corresponds exactly to that of a two-position three-way directional valve, and will be described shortly. Typically, the reservoir 2 takes the form of a compressible container 17 embodied in waterproof material, which is filled with the physiological solution 18 and accommodated internally of a rigid or pressurizable container 19. The interior of the compressible container 17 connects with the supply line 3 in a fluid-tight fit, whereas the pressure container 19 is hermetically sealed in such a way as to create a chamber 20, entirely encompassing the compressible container 17 and in receipt of compressed air from a remote source 21.

Thus, a rise in pressure within the chamber 20 will compress the inner container 17, which in turn collapses and forces physiological solution 18 into the one available route of escape, i.e. the supply line 3.

Alternatively, the compressible container 17 might be omitted, in which case the solution 18 would be invested directly by the compressed air and forced into the supply line 3.

It will be observed from FIG. 1 that the solution line 3 connects with the water circuit 8 at a point upstream of the first branch 9.

With apparatus according to the present invention, it suffices to operate the directional valve 4 to connect the downstream part of the water circuit 8 either with the solution line 3 or with the section of the circuit 8 lying upstream of the valve 4; switching the valve 4 to the reservoir position, the chip blower 10 or a selected instrument 1 will be supplied with solution 18 in place of water, whereupon switching back again restores the water supply.

With the exception of the three-way directional valve 4, the operation of apparatus according to the invention is essentially no different to that of conventional surgery apparatus; considerable advantage is thus gained by users, especially as regards familiarization with the workings of the newer arrangement.

In the embodiment illustrated in FIG. 2, the chip blower 10 is also an instrument of the type enabled for operation by a solenoid valve 5a mounted to the holder T; accordingly, the water and air circuits 8 and 16 for all instruments are controlled by the pedal-operated valves 7 and 7a, and the junction of the solution line 3, directional valve 4 and water circuit 8 occurs upstream of the branch 9, but in this case downstream of the relative pedal valve 7. Provision might be made also for a branch 12 in the air circuit 16, between the relative pedal valve 7a and the chip blower 10, from which to run a line 13 for operation of the reservoir 2. In a preferred version of this embodiment, the line 13 in question will be provided with on-off means 14 interlocked to the three-way direction valve 4 in such a way as to assume the 'on' state whenever the line 3 from the reservoir is activated.

Operation of this embodiment remains substantially the same as in the case of the embodiment of FIG. 1, with the sole difference that the reservoir 2 will be charged with pressure only at the moment when the solution 18 is required; in effect, operating the three-way valve 4 to connect the reservoir 2, the interlocked on-off means 14 will in turn direct compressed air to the chamber 20 when the relative air circuit 16 is activated.

In the embodiment of FIG. 3, the solution dispensing line 3 presents a plurality of branches equivalent in number to the number of instruments 1 to be supplied with the physiological solution 18; each such branch connects with the single water line 6 to a respective instrument 1 at a point downstream of the on-off means 5 (5 V solenoid valve) by which the line is controlled.

Needless to say, the number of three-way valves 4 will be equal to the number of branches, and on-off means 15 (likewise solenoid valves) will also be provided on the solution lines 3a branching to the different instruments 1. Such means 15 operate in the manner of the valves denoted 5, i.e. whenever the handpiece is taken up for use; in short, the three-way valves 4 and the solenoid valves 15 are installed in the holder T. The reservoir 2 can be pressurized by air taken from the instrument supply circuit 16, as in the embodiment of FIG. 2.

In this particular embodiment, the user has only to activate the three-way valve 4 corresponding to a given instrument 1 in order to activate the flow of solution 18, leaving the water or solution lines to the remaining instruments undisturbed.

What is claimed is:

1. A dental surgery system comprising a plurality of dental handpieces, dental holder means (T) for receiving said plurality of dental handpieces, at least one of said handpieces (1) having an air-powered motor and at least one outlet for discharging at least water flow; said system further including a main circuit of combined power-air, and spray-air (16) and a main water supply circuit (8), a plurality of normally closed ON-OFF valves (5b) disposed along single air and single water first supply lines (6b) branched from said main air and water circuits, said first supply lines each carrying the relative fluid to single ones of said plurality of dental handpieces, said normally closed ON-OFF valves (5b) being operable to open the respective first supply lines by removal of the respective handpiece from said dental holder means (T); said at least one powered handpiece controlled by means of said plurality of normally closed ON-OFF valves (5b); a chip blower handpiece (10) provided directly by means of single air and single water second supply lines branched from said main air and water circuits upstream of said first supply line for supplying water and spray air and activated by an ON-OFF valve on each of said second supply lines; the valves on said second supply lines being operable directly by said user; master overall ON-OFF valve means (7, 7a) operable directly by the said user and located in the said main air and water circuits at a point downstream of said second supply lines (6a); a reservoir (2), a medicament (18) disposed within said reservoir (2), a dispensing pipeline (3) communicating at one end with said reservoir (2) and the opposite end of said dispensing pipeline (3) being connected to said main water supply circuit (8) at a point upstream of said second supply line branch (6a); directional control means installed at the juncture of said dispensing pipeline (3) and said main water supply circuit (8) and interlocked to switchable control means (4) in such a way to permit the user to choose between supplying said medicament only and said water only at any one time.

2. A system as claimed in claim 1 wherein said reservoir is provided with a substantially rigid outer container (19) and a flexible sealed inner container (17) with the latter retaining said medicament (18), means for introducing compressed air from a remote source means, such as said main circuit branch (16), into the chamber (20) formed between containers (17) and (19) to cause said medicament (18) to be delivered in a pressurized manner.

3. A dental surgery apparatus comprising at least one powered dental handpiece (1) having an air-powered motor and at least one outlet for discharging at least water flow, said at least one powered dental handpiece being controlled by means of a plurality of normally closed on-off-OFF valves (5b) disposed along single air and single water first supply lines branched from a main circuit of power-air, and spray-air (16), and a main water supply (8) circuit, and carrying the relative fluid to said at least one powered dental handpiece; a chip blower handpiece (10) provided with relative chip blower ON-OFF valves (5a) on single water and single spray-air second supply lines branched from said main air and water circuits, said normally closed ON-OFF valves (5b) and said chip blower ON-OFF valves (5a) being operable to open the respective line by removal of the relative handpiece from a dental holder means (T) forming part of the said dental surgery apparatus; overall ON-OFF means (7, 7a) operable by a user of said apparatus and located on the said main circuit at a point upstream of said first and second supply lines; a reservoir (2) from which a medicament is dispensed into a dispensing pipeline (3) connected to the main water supply circuit (8) at a point between said overall ON-OFF means (7, 7a) and of said first and second supply lines; directional control means installed at the juncture of said dispensing pipeline (3) and said main water supply circuit and interlocked to switchable control means (4) in such a way to permit supplying said medicant only and said water only at any one time.

* * * * *